(12) United States Patent
Henschke et al.

(10) Patent No.: US 9,328,100 B2
(45) Date of Patent: May 3, 2016

(54) PROCESS FOR THE PREPARATION OF β-C-ARYLGLUCOSIDES

(71) Applicant: ScinoPharm Taiwan, Ltd., Tainan (TW)

(72) Inventors: Julian Paul Henschke, Summertown (AU); Ping-Yu Wu, Tainan (TW); Jyh-Hsiung Liao, Hsinchu (TW); Chen-Wei Lin, Chiayi (TW)

(73) Assignee: SCINOPHARM TAIWAN, LTD. (TW)

( * ) Notice: Subject to any disclaimer, the term of this patent is extended or adjusted under 35 U.S.C. 154(b) by 0 days.

(21) Appl. No.: 14/683,883

(22) Filed: Apr. 10, 2015

(65) Prior Publication Data

US 2015/0291569 A1    Oct. 15, 2015

Related U.S. Application Data

(60) Provisional application No. 61/978,454, filed on Apr. 11, 2014.

(51) Int. Cl.
*C07D 409/10* (2006.01)
*C07D 309/10* (2006.01)

(52) U.S. Cl.
CPC ............ *C07D 409/10* (2013.01); *C07D 309/10* (2013.01); *Y02P 20/55* (2015.11)

(58) Field of Classification Search
CPC ........................... C07D 309/10; C07D 409/10
See application file for complete search history.

(56) References Cited

FOREIGN PATENT DOCUMENTS

WO    WO 2013/068850    *  5/2013

* cited by examiner

*Primary Examiner* — Valerie Rodriguez-Garcia
(74) *Attorney, Agent, or Firm* — Sam L. Nguyen; Hamilton, DeSanctis & Cha, LLP

(57) ABSTRACT

The present application discloses a stereoselective process for the preparation of β-C-arylglucosides that does not require the use of conventional carbohydrate protecting groups. In one embodiment, the stereoselective process comprises the preparation of the compound of formula I:

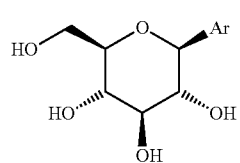

the process comprising: a) contacting 1,6-anhydro-β-D-glucopyranose with a compound of formula II, $R^1R^2R^3Al$, in a solvent to form a first reaction mixture; b) contacting the first reaction mixture of step a) with a second reaction mixture to form a third reaction mixture, wherein the second reaction mixture is prepared by contacting an organoaluminum compound of formula III, $R^4{}_aR^5{}_bAlX_c$, with a compound of formula IV, ArM; and c) contacting the third reaction mixture with a reagent to form the compound of the formula I.

13 Claims, No Drawings

PROCESS FOR THE PREPARATION OF β-C-ARYLGLUCOSIDES

CROSS-REFERENCE TO RELATED APPLICATION

This application claims priority to U.S. Provisional Application No. 61/978,454 filed on Apr. 11, 2014, the complete disclosure of which is incorporated by reference herein.

BACKGROUND OF THE INVENTION

A number of C-glycosides are found in nature and these compounds have been the target of partial or total synthesis. Further, a series of therapeutically effective β-C-arylglucosides (canagliflozin (Ia), dapagliflozin (Ib), ipragliflozin (Ic) and empagliflozin (Id)) that are Sodium-coupled GLucose co-Transporter 2 (SGLT2) inhibitors have recently received marketing approval for the treatment of diabetes active pharmaceutical ingredient. C-Nucleosides are also suitable candidates for use as building blocks of oligonucleotides, for the preparation of natural products and their biologically active derivatives.

While there are different approaches to the preparation of C-arylglycosides, highly efficient methods for their preparation have not yet been realized for certain functionalized β-C-arylglucosides. Synthetic approaches for the preparation of β-C-arylglucosides using organometallics are known in the art, and may include 1,2-addition reactions (see Kraus, G. A.; Molina, M. T. *J. Org. Chem.* 1988, 53, 752-753 and Czernecki, S.; Ville, G. *J. Org. Chem.* 1989, 54, 610-612, for example).

Ineffeciencies known in the art for preparing β-C-arylglucosides include (1) a lack of stereoselectivity during formation of the desired β-anomer of the C-arylglucoside, (2) poor redox economy due to oxidation and reduction reaction steps being required to change the oxidation state of C1, or of C1 and C2, of the carbohydrate moiety, (3) relatively long synthetic routes, (4) the use of toxic metals such as palladium, and/or (5) atom uneconomic protection of hydroxyl groups.

There is a need for a novel, efficient and stereoselective process for the preparation of β-C-arylglucosides.

SUMMARY OF THE INVENTION

Therefore a continuing need exists for novel and efficient methods for the preparation of β-C-arylglucosides, particularly for large scale preparation. The following embodiments, aspects and variations thereof are exemplary and illustrative and are not intended to be limiting in scope.

In one embodiment, there is provided a process for the preparation of the compound of formula I that avoids the use of conventional protecting groups:

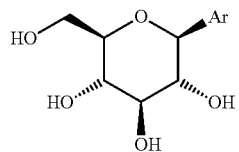
I wherein:
Ar is an aromatic group;
the process comprising:
a) contacting 1,6-anhydro-β-D-glucopyranose with a compound of formula II in a solvent to form a first reaction mixture;

$$R^1R^2R^3Al \qquad \qquad II$$

wherein: $R^1$, $R^2$ and $R^3$ are each independently selected from the group consisting of hydrogen and ($C_1$-$C_{10}$) alkyl;
b) contacting the first reaction mixture of step a) with a second reaction mixture to form a third reaction mixture, wherein the second reaction mixture is prepared by contacting an organoaluminum compound of formula III $$R^4_a R^5_b AlX_c \qquad \qquad III$$

with a compound of formula V:

$$ArM \qquad \qquad IV$$

under conditions sufficient to form the second reaction mixture:
wherein:
the molar ratio of the compound of formula IV over the compound of formula III is below 1 or less than 1;
Ar is an aromatic group;
M is a metal or metal salt;
$R^4$ and $R^5$ are each independently ($C_1$-$C_{10}$) alkyl;
X is selected from the group consisting of I, Br, Cl and F;
a and b are independently numbers ranging from 0-2 where 1≤a+b≤2;
c is a number ranging from 1-2; and
a+b+c=3; and
c) contacting the third reaction mixture with a reagent under condition sufficient to form the compound of formula I in a forth reaction mixture.

In another aspect of the above process, the third reaction mixture is further heated above 100° C. for at least 5 hours. In one variation of the process, the third reaction mixture is heated above 110° C., 120° C., 130° C., 140° C. or above 150° C. In another aspect of the above process, the third reaction mixture is heated for a period of more than about 10 hours, 15 hours, 20 hours or more than about 24 hours. In another aspect of the process, low boiling solvent or solvents may be removed by distillation during the heating of the third reaction mixture. In one aspect of the process, the reaction may be heated at about 125° C. to 135° C. for about 20 to 30 hours. In another aspect of the process, the reaction may be heated at about 100° C. to 150° C. for a sufficient period of time to remove low boiling solvents.

In one aspect of the above process, $R^1$, $R^2$ and $R^3$ are each independently selected from the group consisting of hydrogen and ($C_1$-$C_{10}$) alkyl, where the ($C_1$-$C_{10}$) alkyl group may each be independently a group selected from, for example, methyl, ethyl, propyl, isopropyl, butyl, isobutyl, pentyl and hexyl. In one aspect, $R^1$ and $R^2$ together with the aluminum atom form an aluminum ($C_3$-$C_5$) cycloalkyl group.

In another aspect of the above process, the process further comprises the step of separating the compound of formula I from the forth reaction mixture. In one aspect of the process, the compound of the formula I may be obtained in a purity of at least about 10%, 20%, 25%, 50%, 75%, 85%, 95% and at least about 98% pure by HPLC. In another aspect, the compound of the formula I may be obtained in at least about 10%, at least about 15% yield, at least 35% yield, at least 50% yield, at least 75% yield and at least 85% yield. The separated compound of formula I can be purified by methods known in the art such as crystallisation and column chromatography or by conversion of I to a derivative that can then be purified by methods known in the art. Derivatives of the compound of formula I that are useful for the purification of I include but are not limited to co-crystalline complexes such as disclosed in US Patent Application 2013/0237487 A1 or ester derivatives.

In one aspect of the process, the compound of the formula I obtained is stereoselective and provides the β-anomer with substantially no detectable amounts of the α-anomer, or the compound of the formula I is obtained with only a small amount of the α-anomer, such as less than 5%, less than 1.0%, less than 0.5%, less than 0.25%, less than 0.1% or less than 0.05%, as determined by HPLC. In one aspect, the reaction is highly stereoselective for the formation of the β-anomer, and in some cases, the α-anomer is not be detectable using common analytical techniques (e.g., NMR, HPLC); or may be detectable in only very small amounts (i.e., <1%). In certain aspects, the compound of the formula I is obtained substantially as the pure β-anomer.

In another aspect of the process, M is Li or MgX. In another aspect of the above, X is Cl or Br.

In yet another aspect of each of the above process, Ar is selected from the group consisting of an aromatic ring, an aromatic heterocyclic ring, a biaryl ring system, a fused aromatic ring, a polyaromatic system, and two or more aromatic rings bridged by a methylene group. In an embodiment of this aspect of the invention, I is selected from the group consisting of the β-C-arylglucosides canagliflozin (Ia), dapagliflozin (Ib), ipragliflozin (Ic) and empagliflozin (Id).

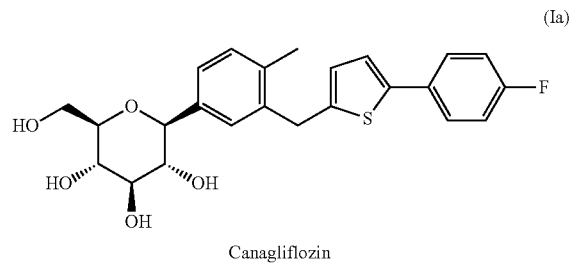

Canagliflozin (Ia)

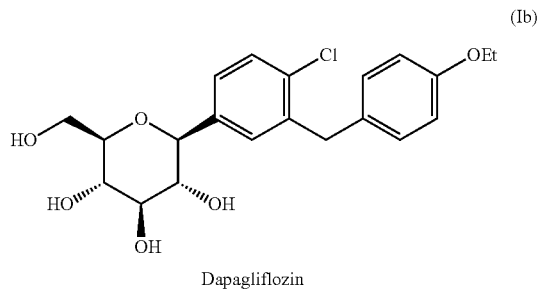

Dapagliflozin (Ib)

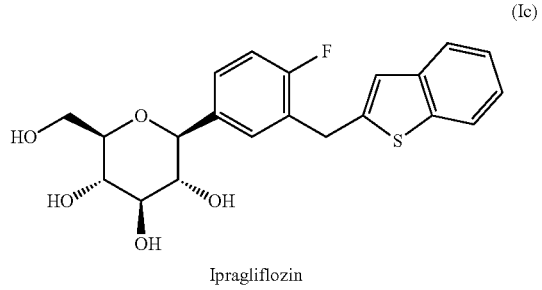

Ipragliflozin (Ic)

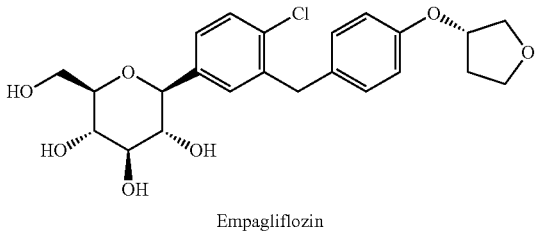

Empagliflozin (Id)

In one aspect of the above process, the reagent of step c is selected from the group consisting of methanol, ethanol, water, aqueous hydrochloric acid, aqueous sulfuric acid, aqueous acetic acid, aqueous tartaric acid, aqueous trifluoroacetic acid, aqueous sodium hydroxide, $Na_2SO_4 \cdot 10H_2O$ (Glauber's salt), aqueous potassium sodium tartrate (Rochelle's salt), aqueous $Na_2SO_4$, and combinations thereof. In one aspect, a non-protic solvent can be added prior to adding of the reagent. Non-protic solvents of this aspect include but are not limited to ethyl acetate, acetone, tetrahydrofuran, 2-methyltetrahydrofuran, methyl tert-butyl ether, $CH_2Cl_2$ and toluene, or a mixture thereof. An inert, insoluble solid material can be added to aid in the removal of the aluminum residues or salts, such as by filtration, that are formed during treatment with the above reagents. Inert, insoluble solid materials of this aspect include but are not limited to diatomaceous earth.

In another aspect of the process, the molar ratio of the compound of formula II to 1,6-anhydro-β-D-glucopyranose is 3:1.

In another aspect of each of the above process, the compound of formula II is selected from the group consisting of $Me_2AlH$, $Et_2AlH$, $—(CH_2)_5Al(H)—$, i-$Bu_2AlH$, t-$Bu_2AlH$, $Me_3Al$, $Et_3Al$, n-$Pr_3Al$, i-$Pr_3Al$, i-$Bu_3Al$ and t-$Bu_3Al$.

In another aspect, the compound of formula III is selected from the group comprising $Me_2AlCl$, $Et_2AlCl$, i-$Bu_2AlCl$, i-Bu(Me)AlCl, i-Bu(Et)AlCl, $EtAlCl_2$ and $MeAlCl_2$.

In another aspect of the above process, Ar is selected from the group consisting of 3-[5-(4-fluorophenyl)thiophen-2-ylmethyl]-4-methylphenyl, 4-chloro-3-(4-ethoxybenzyl)phenyl, 3-(1-benzothien-2-ylmethyl)-4-fluorophenyl, 4-chloro-3-{[4-((3S)-oxolan-3-yl)oxyphenyl]methyl}phenyl, phenyl, naphthyl, pyrrolyl, imidazolyl, pyrazolyl, 2-pyridyl, 3-pyridyl, 4-pyridyl, pyrimidyl, pyrazinyl, pyridazinyl, triazolyl, pyranyl, 2-furyl, 3-furyl, 2-thienyl, 3-thienyl, oxazolyl, isoxazolyl, oxadiazolyl, thiazolyl and thiadiazolyl, each of which may be unsubstituted or substituted by 1 or 2 substituents selected from the group consisting of —F, —Cl, —Br, —I, —$CH_3$, —OH, —SH, —$SCH_3$, —NR'R" (wherein each R' and R" is independently H or —($C_{1-3}$) alkyl), —$OCH_3$, —($C_{1-3}$) alkyl, substituted —($C_{1-3}$) alkyl, -aryl, substituted aryl, heteroaryl and substituted heteroaryl.

In another embodiment, there is provided a composition (carbohydrate-aluminum mixture) prepared by a process comprising:

contacting 1,6-anhydro-β-D-glucopyranose with a compound of the formula II to form a reaction mixture;

$$R^1R^2R^3Al \qquad \qquad II$$

wherein:

$R^1$, $R^2$ and $R^3$ are each independently selected from the group consisting of hydrogen and ($C_1$-$C_{10}$) alkyl; under conditions sufficient to form the composition.

In some cases, the molar ratio of the compound of formula II to 1,6-anhydro-β-D-glucopyranose is 3:1.

In addition to the exemplary embodiments, aspects and variations described above, further embodiments, aspects and variations will become apparent by reference to the drawings and figures and by examination of the following descriptions.

The foregoing examples of the related art and limitations are intended to be illustrative and not exclusive. Other limitations of the related art will become apparent to those of skill in the art upon a reading of the specification and a study of the drawings or figures as provided herein.

DETAILED DESCRIPTION OF THE INVENTION

Definitions

Unless specifically noted otherwise herein, the definitions of the terms used are standard definitions used in the art of organic synthesis and pharmaceutical sciences. Exemplary embodiments, aspects and variations are illustrated in the figures and drawings, and it is intended that the embodiments, aspects and variations, and the figures and drawings disclosed herein are to be considered illustrative and not limiting.

An "alkyl" group is a straight, branched, saturated or unsaturated, aliphatic group having a chain of carbon atoms, optionally with oxygen, nitrogen or sulfur atoms inserted between the carbon atoms in the chain or as indicated. A $(C_1-C_{20})$ alkyl, for example, includes alkyl groups that have a chain of between 1 and 20 carbon atoms, and include, for example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, penta-1,4-dienyl, hexa-1,3-dienyl, hexa-1,3,5-trienyl, and the like. A variable or substituent, such as $R^1$, $R^2$, $R^3$, $R^4$, $R^5$ that is defined as a $(C_1-C_{10})$alkyl group means, for example, that each of the R groups can be independently defined by any one of the $(C_1-C_{10})$ alkyl groups, and can be the same group or different groups. For example, the $R^4$ group may be a methyl or ethyl group, and the $R^5$ group may be an ethyl or propyl group etc. . . . An alkyl group may also be represented, for example, as a —$(CR^1R^2)_m$— group where $R^1$ and $R^2$ are independently hydrogen or are independently absent, and for example, m is 1 to 8, and such representation is also intended to cover both saturated and unsaturated alkyl groups.

An alkyl as noted with another group such as an aryl group, represented as "arylalkyl" for example, is intended to be a straight, branched, saturated or unsaturated aliphatic divalent group with the number of atoms indicated in the alkyl group (as in $(C_1-C_{20})$ alkyl, for example) and/or aryl group (as in $(C_5-C_{14})$ aryl, for example) or when no atoms are indicated means a bond between the aryl and the alkyl group. Nonexclusive examples of such group include benzyl, phenethyl and the like.

An "alkylene" group is a straight, branched, saturated or unsaturated aliphatic divalent group with the number of atoms indicated in the alkyl group; for example, a —$(C_1-C_3)$ alkylene- or —$(C_1-C_3)$ alkylenyl-.

An "aryl" group or an "aromatic" group as used herein, refers to a radical derived from an aromatic hydrocarbon by removal of one hydrogen, such as phenyl, or naphthyl (or naphthalenyl), and includes heteroaryl groups. Representative aryl groups may include, for example, an aromatic ring, an aromatic heterocyclic ring, a biaryl ring system, a fused aromatic ring, a polyaromatic system, and two or more aromatic rings bridged by a methylene group.

Representative aryl groups may also include, for example:

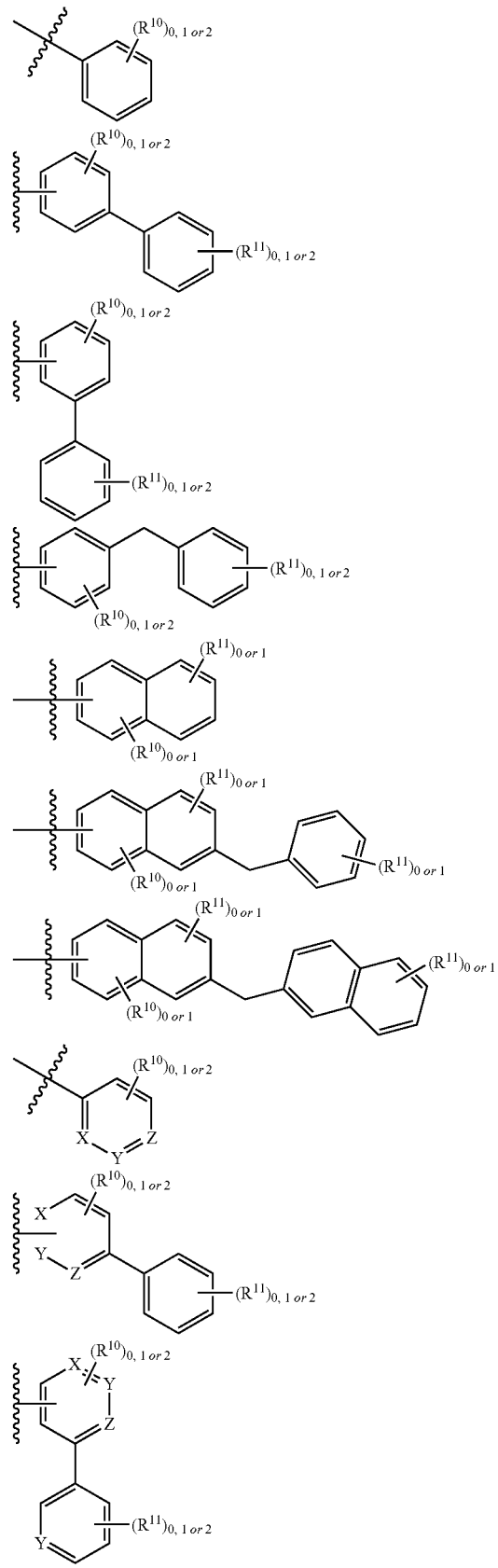

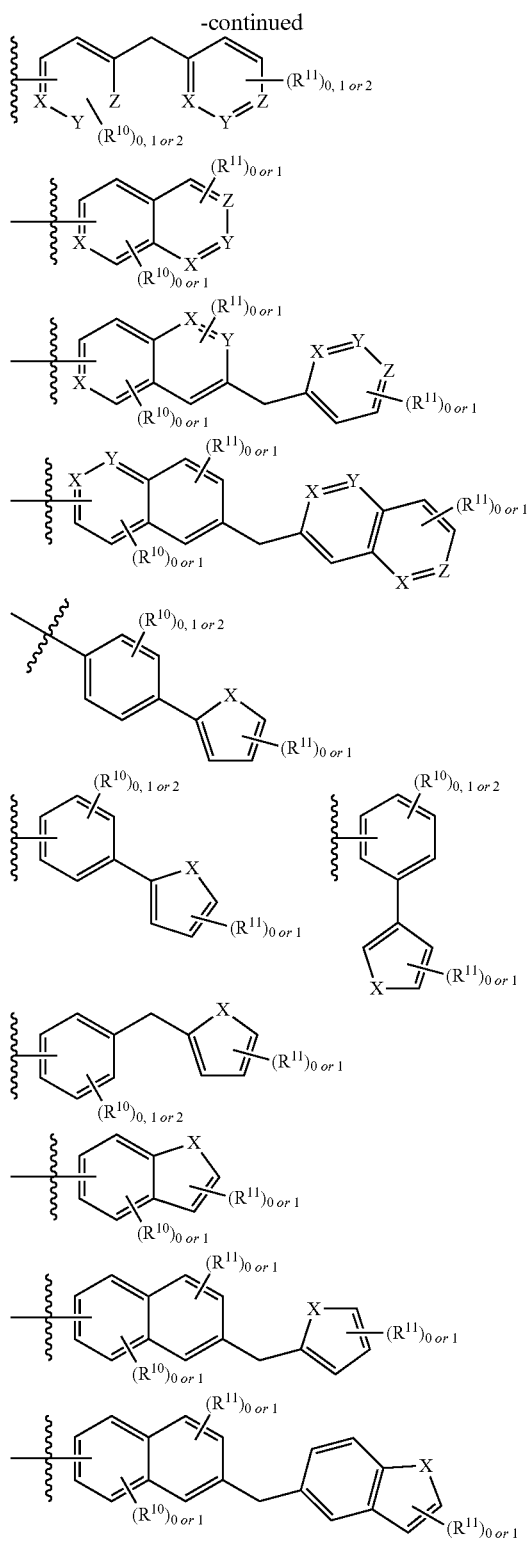

wherein $R^{10}$ and $R^{11}$, when present, are each independently a substituent selected from the group consisting of —F, —Cl, —Br, —I, —CH$_3$, —OH, —SH, —SCH$_3$, —NH$_2$, NHR', —NR'R" (wherein each R' is independently H or —(C$_{1-3}$) alkyl), —CN, —NO$_2$, —OCH$_3$, —(C$_{1-3}$)alkyl, substituted —(C$_{1-3}$)alkyl, -aryl, substituted aryl, heteroaryl and substituted heteroaryl; and X, Y and Z are each independently —CH— or N, provided that at least one of X, Y and Z is N; and X is O, S or NH when X is a divalent group in the ring.

A "carbohydrate" as used herein refers to a sugar such as arabinose, lyxose, ribose, xylose, ribulose, xylulose, allose, altrose, galactose, glucose, gulose, idose, mannose, talose, fructose, mannoheptulose, sedoheptulose, octolose and sialose and/or modified saccharides, such as, for example, 2'-fluororibose, 2'-deoxyribose and hexose.

A "cyclyl" such as a monocyclyl or polycyclyl group includes monocyclic, or linearly fused, angularly fused or bridged polycycloalkyl, or combinations thereof. Such cyclyl group is intended to include the heterocyclyl analogs. A cyclyl group may be saturated, partially saturated or aromatic.

"Halogen" or "halo" means fluorine, chlorine, bromine or iodine.

The term "heteroaryl" as used herein, refers to a radical derived from an aromatic mono- or bicyclic ring system, in which 1, 2, 3, 4 or 5 carbon atoms are replaced by heteroatoms selected from nitrogen (N), oxygen (O) and sulfur (S), wherein N includes ring nitrogen atoms which carry a hydrogen atom or a substituent, or ring nitrogen atoms which do not carry a hydrogen atom or a substituent. Ring heteroatoms can be located in any position and provided that the heterocyclic system or ring that is stable. Heteroaryl radicals are derived from 5-membered or 6-membered monocyclic rings or 8-membered, 9-membered or 10-membered bicyclic rings. Such aryl rings may include 5-membered or 6-membered monocyclic rings, 9-membered or 10-membered bicyclic rings, or 5-membered or 6-membered monocyclic rings.

The term "heterocyclyl" or "heterocycle" is a cycloalkyl radical wherein one or more of the atoms forming the ring is a heteroatom that is a N, O or S. Such terms also include heteroaryl radicals. Examples of heteroaryl radicals include unsaturated 5 to 6 membered hetero-monocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl, such as 4H-1,2,4-triazolyl, 1H-1,2,3-triazolyl, 2H-1,2,3-triazolyl; unsaturated 5- to 6-membered hetero-monocyclic group containing an O atom, such as pyranyl, 2-furyl, 3-furyl, etc.; unsaturated 5 to 6-membered hetero-monocyclic group containing an S atom, such as 2-thienyl, 3-thienyl, etc.; unsaturated 5- to 6-membered hetero-monocyclic group containing 1 to 2 O atoms and 1 to 3 N atoms, such as oxazolyl, isoxazolyl, oxadiazolyl, including 1,2,4-oxadiazolyl, 1,3,4-oxadiazolyl, 1,2,5-oxadiazolyl; unsaturated 5 to 6-membered hetero-monocyclic group containing 1 to 2 S atoms and 1 to 3 N atoms, such as thiazolyl, thiadiazolyl, including 1,2,4-thiadiazolyl, 1,3,4-thiadiazolyl, 1,2,5-thiadiazolyl. Further, non-exclusive examples of heterocyclyl include piperidyl, 4-morpholyl, 4-piperazinyl, pyrrolidinyl, 1,4-diazaperhydroepinyl, 1,3-dioxanyl and the like.

The term "heteroaryl" such as a heteroaryl radical, used alone or in combination with another group, refers to fully unsaturated heteroatom-containing ring radicals, where the heteroatoms may be selected from N, S and O.

In addition, the terms "heterocycle" and "heteroaryl" also include radicals which are fused or condensed with aryl radicals, including unsaturated condensed heterocyclic or heteroaryl groups containing 1 to 5 N atoms (such as indolyl, isoindolyl, indolizinyl, benzimidazolyl, quinolyl, isoquinolyl, indazolyl, benzotriazolyl, tetrazolopyridazinyl); unsaturated condensed heterocyclic group containing 1 to 2 O atoms and 1 to 3 N atoms such as benzoxazolyl, benzoxadiazolyl; unsaturated condensed heterocyclic group containing 1 to 2 S atoms and 1 to 3 N atoms, such as benzothiazolyl, benzothiadiazolyl; and saturated, partially unsaturated and unsaturated condensed heterocyclic group containing 1 to 2 O or S atoms, such as benzofuryl, benzothienyl, 2,3-dihydrobenzo[1,4]dioxinyl and dihydrobenzofuryl. Examples of heterocyclic radicals include five to ten membered fused or unfused radicals. Further examples of heteroaryl radicals include quinolyl, isoquinolyl, imidazolyl, pyridyl, thienyl, thiazolyl, oxazolyl, furyl and pyrazinyl. Other examples of heteroaryl radicals are 5- or 6-membered heteroaryl containing one or two heteroatoms selected from S, N and O, such as thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl radicals. Examples of non-nitrogen containing heteroaryl include, without limitation, pyranyl, 2-furyl, 3-furyl, 2-thienyl, 3-thienyl, benzofuryl, benzothienyl etc.

"Substituted or unsubstituted" or "optionally substituted" means that a group such as, for example, alkyl, aryl, heterocyclyl, ($C_1$-$C_8$) cycloalkyl, hetrocyclyl ($C_1$-$C_8$) alkyl, aryl ($C_1$-$C_8$) alkyl, heteroaryl, heteroaryl ($C_1$-$C_8$) alkyl, and the like, unless specifically noted otherwise, may be unsubstituted or, may substituted by 1, 2 or 3 substitutents selected from the group such as halo, nitro, trifluoromethyl, trifluoromethoxy, methoxy, carboxy, —$NH_2$, —OH, —SH, —$NHCH_3$, —$N(CH_3)_2$, —SMe, cyano and the like.

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, conventional protective groups may be introduced into the aromatic group and finally removed. Suitable protective groups for amino, hydroxy, and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989. However, in this invention, protection of the hydroxyl groups of the 1,6-anhydro-β-D-glucopyranose prior to reaction is not required.

In one variation, the compounds of this invention can be prepared by the general processes and steps outlined in Scheme I, below:

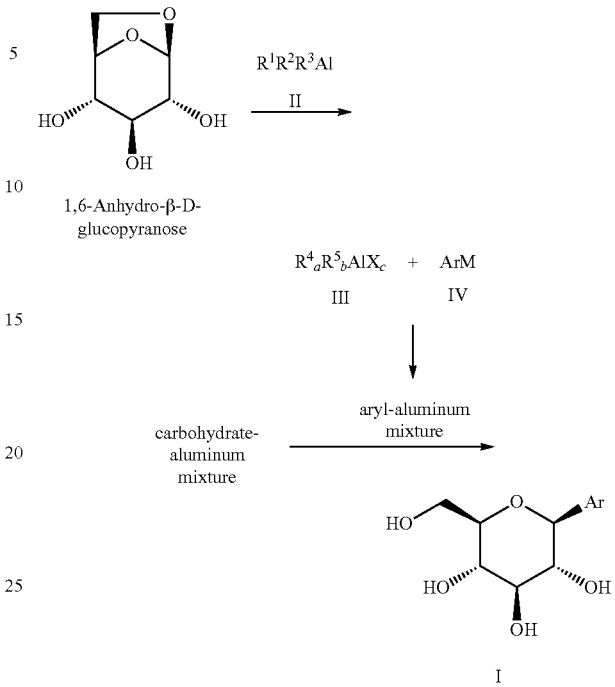

In one embodiment, a 1,6-anhydro-β-D-glucopyranose is contacted with an organoaluminum compound, such as a compound $R^1R^2R^3Al$, wherein Al is aluminum and $R^1$, $R^2$ and $R^3$ are each independently selected from the group consisting of hydrogen and ($C_1$-$C_{10}$)alkyl, to form a carbohydrate-aluminum complex (or compound) mixture or mixture of carbohydrate-aluminum complexes (or compounds). The reaction may be performed in a solvent or solvent mixture, such as an organic solvent selected from the group consisting of diethyl ether, diisopropyl ether, tetrahydrofuran, 2-methyltetrahydrofuran, dioxane, benzonitrile, di-butyl ether, toluene, chlorobenzene, dichlorobenzene, anisole, petroleum ether, hexane, hexanes and heptane or mixtures thereof. In one embodiment, the reaction may be performed below room temperature, at about 0° C., at about –10° C., –25° C., –50° C. or at about –65° C. The reaction mixture may be warmed to about room temperature and stirred until the reaction is complete. The formation of the resulting carbohydrate-aluminum mixture is conducted as a non-conventional means of protecting the hydroxyl groups of the carbohydrate moiety from reaction with the aryl-aluminum mixture in step b. This non-conventional approach to protecting the hydroxyl groups of the carbohydrate moiety is conducted in situ in step a and does not require isolation of the resulting carbohydrate-aluminum mixture and is therefore more convenient and can be more cost efficient that other approaches to the synthesis of β-C-arylglucosides that require the use of conventional protecting groups.

The resulting carbohydrate-aluminum mixture is then contacted with an aryl-aluminum mixture or compound that is prepared by the addition of an aluminum halide compound, such as $R^4R^5AlX$, with an aryl metal, such as ArLi (an aryl-lithium reagent) or ArMgX (a Grignard reagent). ArLi and ArMgX are well-known in the literature and can be readily prepared from the corresponding aryl halide compounds, ArX. Some ArLi and ArMgX compounds are commercially available. The carbohydrate-aluminum mixture may be contacted with the aryl-aluminum mixture under condition sufficient to provide a β-C-arylglucoside compound. In one aspect, the reaction mixture may be stirred at room temperature or above room temperature for a period of time sufficient to complete the reaction. In one aspect, the reaction mixture may be heated above room temperature, such as about 35° C., about 50° C., about 75° C., 85° C., 100° C., 125° C. or about 150° C. or higher, for a sufficient period of time until the reaction is determined to be complete or no further reaction occurs. In one aspect, the reaction mixture may be heated for at least about 5 hours, 8 hours, 10 hours, 15 hours, 20 hours, 24 hours, or about 30 hours. The reaction mixture may be treated with an alcohol, such as methanol, or ethanol, aqueous hydrochloric acid, aqueous trifluoroacetic acid and water, or mixtures thereof, and the reaction may be worked up in the usual manner. The β-C-arylglucoside compound may be isolated from the reaction in about 10% to about 85% yield. In one embodiment of the current invention, the molar ratio of the compound of formula IV to 1,6-anhydro-β-D-glucopyranose is from 1:1 to 1:2. In general, the aromatic compound of formula IV is more expensive than 1,6-anhydro-β-D-glucopyranose. This invention provides an approach that nearly one equivalent excess of 1,6-anhydro-β-D-glucopyranose with respect to the compound of formula IV can be used for the preparation of the compound of formula I. Therefore, this approach is more cost effective for industrial manufacturing of the compound of formula I since the amount of compound of formula IV is reduced. In one embodiment of the current invention, the molar ratio of the compound of formula IV over the compound of formula III is below 1. Preferably, the molar ratio of the compound of formula IV over the compound of formula III is about 0.6. With the use of the aryl-aluminum mixture prepared in the ratio as described above, the compound of I can be obtained in the yield of 20~40% with respect to the compound of formula IV.

EXAMPLE 1

Synthesis of 1-C-phenyl-β-D-glucopyranoside

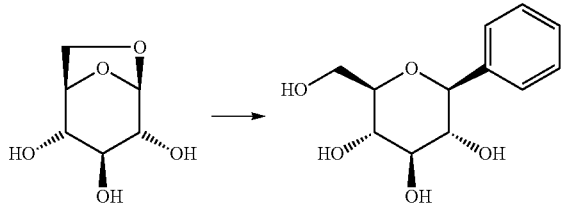

To diisobutylaluminum chloride (5 mL, 4.0 mmol, 0.8 M in n-heptane) in anisole (6.0 mL) was added phenyl lithium (0.9 mL, 1.1 mmol, 1.2 M in n-butyl ether) dropwise at 0° C. and stirred at ambient temperature overnight. To a suspension of 1,6-anhydro-β-D-glucopyranose (248 mg, 1.5 mmol) in anisole (4.0 mL) at 0° C. was added dropwise diisobutylaluminum hydride (3.0 mL, 3 mmol, 1.0 M in toluene) and then was stirred at ambient temperature overnight.

This solution was then added to the above prepared aluminum mixture via syringe. The mixture was concentrated under reduced pressure at ambient temperature to remove low-boiling point solvents.

The remaining mixture (comprising anisole/di-n-butyl ether/toluene as solvent) was heated at 113-117° C. (internal temperature) for 20 hours. An aliquot of the product mixture was diluted with 5% trifluoroacetic acid in methanol, was left to stand for at least 5 minutes and was then analyzed by HPLC. HPLC assay analysis indicated a 27% yield of 1-C-phenyl-β-D-glucopyranoside had been achieved.

$^1$H NMR (400 MHz, CD$_3$OD) δ 7.46-7.43 (m, 2H), 7.37-7.28 (m, 3H), 4.16 (d, J=9.2 Hz, 1H), 3.92-3.89 (m, 1H), 3.75-3.70 (m, 1H), 3.53-3.38 (m, 4H); $^{13}$C NMR (100 MHz, CD$_3$OD) δ 139.5 (C), 127.7 (CH×2), 127.62 (CH×2), 127.55 (CH), 82.3 (CH), 80.8 (CH), 78.4 (CH), 75.0 (CH), 70.6 (CH), 61.8 (CH$_2$); LCMS (ESI) m/z 258 (100, [M+NH$_4$]$^+$), 263 (69, [M+Na]$^+$), 503 (25, [2M+Na]$^+$).

EXAMPLE 2

Synthesis of canagliflozin (Ia) (1-C-(3-((5-(4-fluorophenyl)thiophen-2-yl)methyl)-4-methylphenyl)-β-D-glucopyranoside)

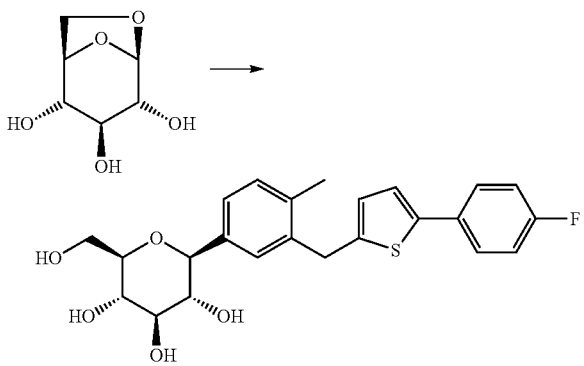

To a solution of 2-(5-bromo-2-methylbenzyl)-5-(4-fluorophenyl)thiophene (796 mg, 2.2 mmol) in 2-methyltetrahydrofuran (20 mL) was added dropwise n-butyl lithium (1.63 mL, 2.6 mmol, 1.6 M in hexane) at −76° C. and was then stirred for 30 min. Diisobutylaluminum chloride (4.4 mL, 3.5 mmol, 0.8 M in n-heptane) was added and the mixture was stirred for 1 hour and then warmed to ambient temperature and was stirred overnight. To a suspension of 1,6-anhydro-β-D-glucopyranose (648 mg, 4.0 mmol) in anisole (10 mL) at 0° C. was added dropwise diisobutylaluminum hydride (12 mL, 12 mmol, 1.0 M in toluene) and was then stirred at ambient temperature overnight. This solution was then added to the above prepared aluminum mixture via syringe. The mixture was distilled (external bath temperature was 158° C.) to remove the low-boiling solvents. To the remaining mixture was added anisole (10 mL) and the mixture was heated (external bath temperature was 158° C.) for 22 hours at which time HPLC assay analysis indicated a 42% yield of 1-C-(3-((5-(4-fluorophenyl)thiophen-2-yl)methyl)-4-methylphenyl)-β-D-glucopyranoside.

After cooling to 0° C., ethyl acetate (60 mL) was added to the reaction followed by methanol (1.0 mL), and followed by 3 N HCl (10.0 mL) for neutralization. The organic portion was separated and concentrated.

The crude product was purified by column chromatography (eluting with 1:10 methanol/CH$_2$Cl$_2$) affording 1-C-(3-((5-(4-fluorophenyl)thiophen-2-yl)methyl)-4-methylphenyl)-β-D-glucopyranoside (363 mg, 37%) as white solid.

$^1$H NMR (400 MHz, DMSO-d$_6$) δ 7.63-7.57 (m, 2H), 7.28 (d, J=3.6 Hz, 1H), 7.23-7.18 (m, 3H), 7.17-7.12 (m, 2H), 6.80 (d, J=3.6 Hz, 1H), 4.93 (br, 2H, OH), 4.73 (br, 1H, OH), 4.44 (br, 1H, OH), 4.16 (d, J=16 Hz, 1H), 4.10 (d, J=16 Hz, 1H), 3.97 (d, J=9.2 Hz, 1H), 3.71 (d, J=11.6 Hz, 1H), 3.47-3.43 (m,

1H), 3.30-3.15 (m, 4H), 2.27 (s, 3H); $^{13}$C NMR (100 MHz, DMSO-d$_6$) δ 161.8 (d, J=243 Hz, C), 144.1 (C), 140.7 (C), 138.7 (C), 137.8 (C), 135.4 (C), 131.0 (d, J=3.1 Hz, C), 130.1 (CH), 129.5 (CH), 127.4 (d, J=8.1 Hz, CH×2), 126.8 (CH), 126.7 (CH), 123.9 (CH), 116.4 (d, J=21.6 Hz, CH×2), 81.8 (CH), 81.7 (CH), 79.0 (CH), 75.2 (CH), 70.9 (CH), 61.9 (CH$_2$), 33.9 (CH$_2$), 19.3 (CH$_3$); LCMS (ESI) m/z 462 (100, [M+NH$_4$]$^+$), 467 (3, [M+Na]$^+$).

EXAMPLE 3

Synthesis of 1-C-(3-(tert-butyl-diphenyl-silanyloxymethyl)-4-methyl-phenyl)-β-D-glucopyranoside

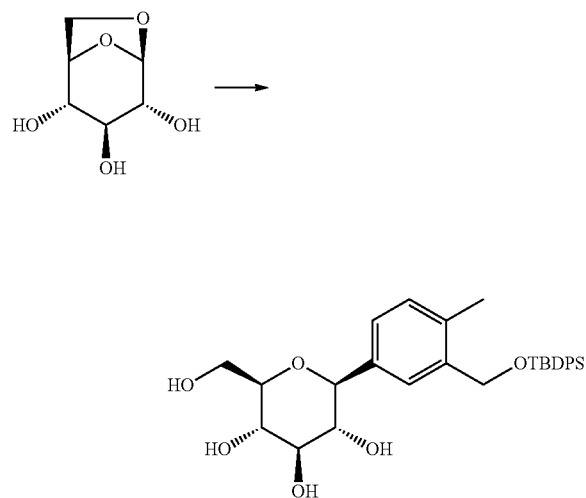

To a solution of (5-bromo-2-methyl-benzyloxy)-tert-butyl-diphenyl-silane (967.2 mg, 2.2 mmol) in 2-methyltetrahydrofuran (20 mL) was added dropwise with n-butyl lithium (1.63 mL, 2.6 mmol, 1.6 M in hexane) at −76° C. and stirred for 3.0 h. Diisobutylaluminum chloride (4.4 mL, 3.5 mmol, 0.8 M in n-heptane) was added and the mixture was stirred for 1 hour and warmed to ambient temperature and stirred overnight. To a suspension of 1,6-anhydro-β-D-glucopyranose (648 mg, 4.0 mmol) in anisole (10 mL) at 0° C. was added dropwise diisobutylaluminum hydride (12 mL, 12 mmol, 1.0 M in toluene) and was then stirred at ambient temperature overnight. This solution was then added to the above prepared aluminum mixture via syringe. The mixture was distilled (external bath temperature was 158° C.) to remove the low-boiling solvents (35 mL of volatiles was removed). To the remaining mixture was added anisole (10 mL) and the mixture was heated (external bath temperature was 158° C.) for 22 hours.

After cooling to 0° C., ethyl acetate (60 mL) was added to the reaction followed by methanol (1.0 mL), and followed by 3 N HCl (10.0 mL) for neutralisation. The organic portion was separated and concentrated. The crude product was purified by column chromatography (eluting with 1:15 methanol/ CH$_2$Cl$_2$) affording 1-C-(3-(tert-butyldiphenylsilyloxymethyl)-4-methylphenyl)-β-D-glucopyranoside (181 mg, 16%).

$^1$H NMR (400 MHz, CD$_3$OD) δ 7.70 (m, 4H), 7.52-7.37 (m, 7H), 7.28-7.13 (m, 2H), 4.76 (s, 2H), 4.19 (d, J=9.2 Hz, 1H), 3.93 (dd, J=12, 3.2 Hz, 1H), 3.83 (dd, J=12, 4.8 Hz, 1H), 3.71 (m, 2H), 3.50 (m, 2H), 2.20 (s, 3H), 1.11 (s, 9H).

EXAMPLE 4

Synthesis of canagliflozin (Ia) (1-C-(3-((5-(4-fluorophenyl)thiophen-2-yl)methyl)-4-methylphenyl)-β-D-glucopyranoside)

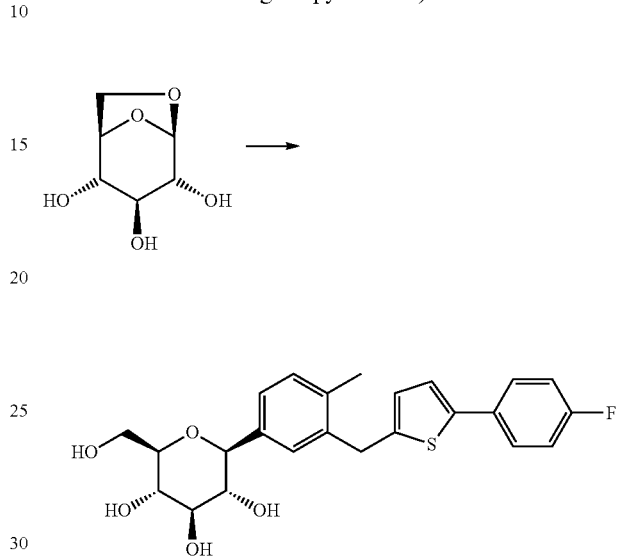

To a solution of 2-(5-bromo-2-methylbenzyl)-5-(4-fluorophenyl)thiophene (316.0 g, 0.88 mol) in toluene (2.48 Kg) and diisopropyl ether (1.03 Kg) was added dropwise n-butyl lithium (480 g, 1.75 mol, 2.5 M in hexane) at 0° C. and was then stirred for 30 min. Diisobutylaluminum chloride (1.27 Kg, 1.4 mol, 0.8 M in n-heptane) was added and the mixture was stirred for 1 hour and then warmed to 20-25° C. and was stirred for 12 hours. To a suspension of 1,6-anhydro-β-D-glucopyranose (255.5 g, 1.57 mol) in anisole (4.7 Kg) and toluene (2.0 Kg) at 0° C. was added dropwise diisobutylaluminum hydride (4.05 Kg, 4.72 mol, 1.0 M in toluene) and was then stirred at 5-15° C. for 1 h and at 20-25° C. for 8 h. This solution was then added to the above prepared aluminum mixture via cannula. The mixture was distilled at 100-130° C. at ambient pressure to remove the low-boiling solvents. The mixture was heated at 125-135° C. for 28 hours at which time HPLC assay analysis indicated a 27% yield of 1-C-(3-((5-(4-fluorophenyl)thiophen-2-yl)methyl)-4-methylphenyl)-β-D-glucopyranoside.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

The entire disclosures of all documents cited throughout this application are incorporated herein by reference.

What is claimed is:

1. A process for the preparation of the compound of formula I:

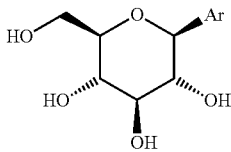

I wherein:
Ar is an aromatic group;
the process comprising:
a) contacting 1,6-anhydro-β-D-glucopyranose with a compound of formula II in a solvent to form a first reaction mixture;

$$R^1R^2R^3Al \qquad II$$

wherein:
R$^1$, R$^2$ and R$^3$ are each independently selected from the group consisting of hydrogen and (C$_1$-C$_{10}$) alkyl;
b) contacting the first reaction mixture of step a) with a second reaction mixture to form a third reaction mixture, wherein the second reaction mixture is prepared by contacting an organoaluminum compound of formula III $$R^4_aR^5_bAlX_c \qquad III$$

with a compound of formula IV:

$$ArM \qquad IV$$

to form the second reaction mixture:
wherein:
the molar ratio of the compound of formula IV over the compound of formula III is below 1;
Ar is as defined above;
M is a metal or metal salt;
W and R$^5$ are each independently (C$_1$-C$_{10}$) alkyl;
X is selected from the group consisting of I, Br, Cl and F;
a and b are independently integers ranging from 0-2 where 1≤a+b≤2;
c is an integer ranging from 1-2; and
a+b+c=3; and
c) contacting the third reaction mixture with a neutralizing reagent to form the compound of the formula I in a fourth reaction mixture.

2. The process according to claim 1, wherein the third reaction mixture in step b) is further heated above 100° C. for at least 5 hours.

3. The process according to claim 1, wherein M is Li or MgX.

4. The process according to claim 1 or 3, wherein X is Cl or Br.

5. The process according to claim 1, wherein Ar is selected from the group consisting of an aromatic hydrocarbon, an aromatic heterocyclic ring, a biaryl ring system, a fused aromatic ring, a polyaromatic system, and two or more aromatic rings bridged by a methylene group.

6. The process according to claim 1, wherein the reagent of step c) is selected from the group consisting of methanol, ethanol, water, aqueous hydrochloric acid, aqueous trifluoroacetic acid, aqueous sulfuric acid, aqueous acetic acid, aqueous tartaric acid, aqueous sodium hydroxide, Na$_2$SO$_4$.10H$_2$O (Glauber's salt), aqueous potassium sodium tartrate (Rochelle's salt), aqueous Na$_2$SO$_4$, and combinations thereof.

7. The process according to claim 1, wherein the molar ratio of the compound of formula II to 1,6-anhydro-β-D-glucopyranose is 3:1.

8. The process according to claim 1, wherein the molar ratio of the compound of formula IV to 1,6-anhydro-β-D-glucopyranose is from 1:1 to 1:2.

9. The process according to claim 1, wherein the compound of formula II is selected from the group consisting of Me$_2$AlH, Et$_2$AlH, —(CH$_2$)$_5$Al(H)—, i-Bu$_2$AlH, t-Bu$_2$AlH, Me$_3$Al, Et$_3$Al, n-Pr$_3$Al, i-Pr$_3$Al, i-Bu$_3$Al and t-Bu$_3$Al.

10. The process according to claim 1, wherein the compound of formula III is selected from the group consisting of Me$_2$AlCl, Et$_2$AlCl, i-Bu$_2$AlCl, i-Bu(Me)AlCl, i-Bu(Et)AlCl, EtAlCl$_2$ and MeAlCl$_2$.

11. The process according to claim 1, wherein Ar is selected from the group consisting of 3-[5-(4-fluorophenyl)thiophen-2-ylmethyl]-4-methylphenyl, 4-chloro-3-(4-ethoxybenzyl)phenyl, 3-(1-benzothien-2-ylmethyl)-4-fluorophenyl, 4-chloro-3-{[4-((3S)-oxolan-3-yl)oxyphenyl]methyl}phenyl, phenyl, naphthyl, pyrrolyl, imidazolyl, pyrazolyl, 2-pyridyl, 3-pyridyl, 4-pyridyl, pyrimidyl, pyrazinyl, pyridazinyl, triazolyl, 2 furyl, 3-furyl, 2-thienyl, 3-thienyl, oxazolyl, isoxazolyl, oxadiazolyl, thiazolyl and thiadiazolyl, each of which may be unsubstituted or substituted by 1 or 2 substituents selected from the group consisting of —F, —Cl, —Br, —I, —CH$_3$, —OH, —SH, —SCH$_3$, —NR'R" (wherein each R' is independently H or —(C$_{1-3}$) alkyl), —OCH$_3$, —(C$_{1-3}$)akyl, substituted —(C$_{1-3}$)akyl, -aryl, substituted aryl, heteroaryl and substituted heteroaryl.

12. The process according to claim 1, wherein the compound of formula I is selected from the group consisting of canagliflozin (Ia), dapagliflozin (Ib), ipragliflozin (Ic) and empagliflozin (Id).

13. A composition prepared by a process of:
contacting 1,6-anhydro-β-D-glucopyranose with a compound of formula II to form a reaction mixture;

$$R^1R^2R^3Al \qquad II$$

wherein:
R$^1$, R$^2$ and R$^3$ are each independently selected from the group consisting of hydrogen and (C$_1$-C$_{10}$) alkyl;
wherein the molar ratio of the compound of formula II to 1,6-anhydro-β-D-glucopyranose is 3:1.

* * * * *